United States Patent [19]
Allinson

[11] 4,262,662
[45] Apr. 21, 1981

[54] PENILE SUPPORT

[76] Inventor: Francis W. Allinson, 53 W. Lewis Ave., Phoenix, Ariz. 85003

[21] Appl. No.: 82,958

[22] Filed: Oct. 9, 1979

Related U.S. Application Data

[63] Continuation-in-part of Ser. No. 12,836, Jan. 16, 1979, which is a continuation-in-part of Ser. No. 970,490, Dec. 18, 1978, abandoned.

[51] Int. Cl.³ .............................................. A61F 5/00
[52] U.S. Cl. ..................................................... 128/79
[58] Field of Search ......................................... 128/79

[56] References Cited

U.S. PATENT DOCUMENTS 3,920,007  11/1975  Fine ......................................... 128/79

FOREIGN PATENT DOCUMENTS

| 112737 | 4/1929 | Australia ..................................... | 128/79 |
| 368352 | 3/1923 | Fed. Rep. of Germany ............. | 128/79 |
| 831874 | 2/1952 | Fed. Rep. of Germany ............. | 128/79 |
| 711544 | 6/1931 | France ........................................ | 128/79 |
| 60397  | 7/1912 | Switzerland ............................... | 128/79 |
| 589978 | 2/1978 | U.S.S.R. .................................... | 128/79 |

Primary Examiner—John D. Yasko

[57] ABSTRACT

A malleable clip-on self-retaining endless outline penile support used to make the sexual act possible in the case of male weakness. The device consists of a malleable adjustable distal head piece, joined by two less malleable ventral longitudinal supports which unite proximally with a generally looped proximal portion. The malleability of the proximal looped portion enables adjustment transversely of the proximal ends of the longitudinal supports, and a malleable angle towards the proximal end of each longitudinal support enables adjustment in length of the penile support to be made. Additional fixation, distally and proximally may be made by an elastic member. The support may be encased in plastic. The proximal looped shape portion can also be made of malleable wire whose free distal ends fit into the proximal ends of tubular longitudinal supports making further adjustment in length possible.

1 Claim, 18 Drawing Figures

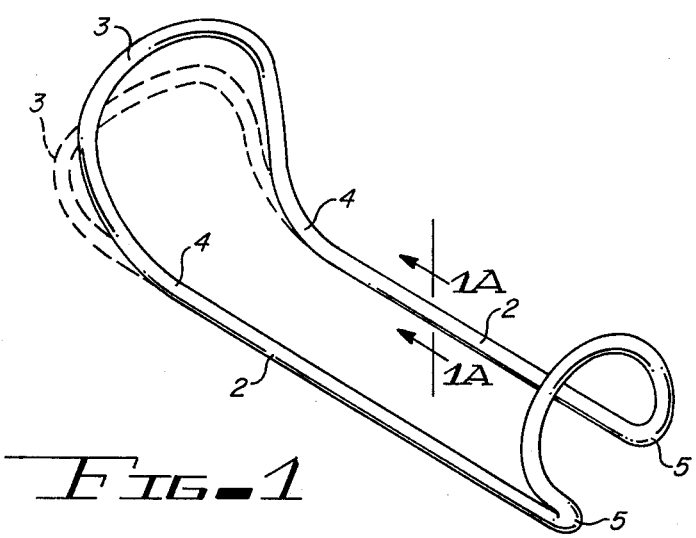
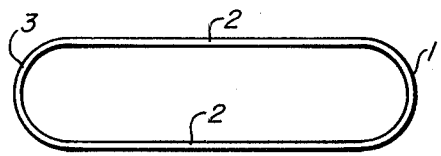
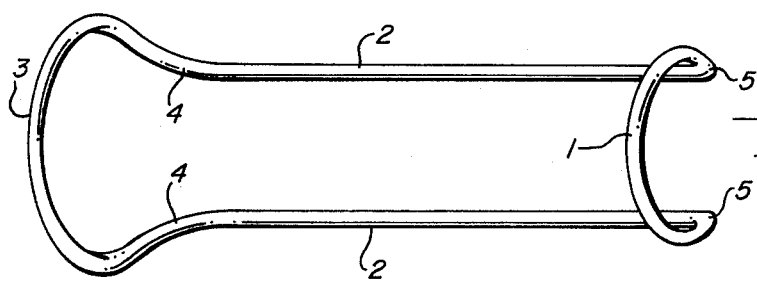
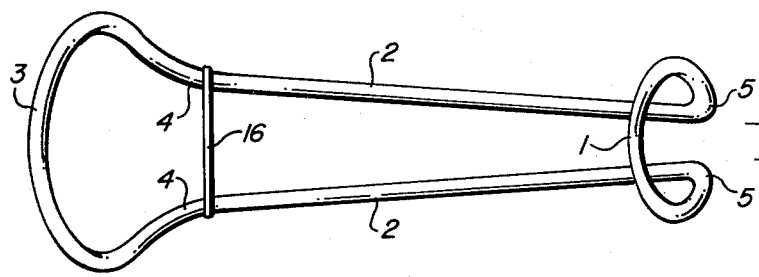
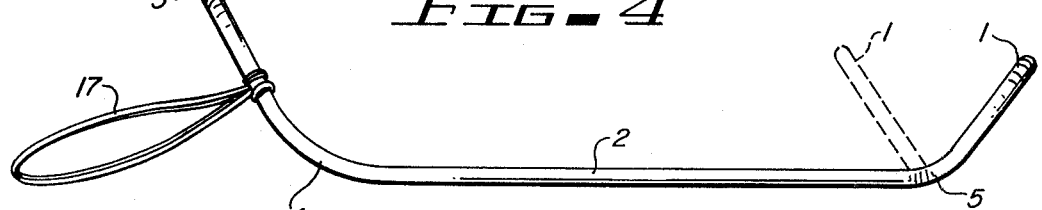
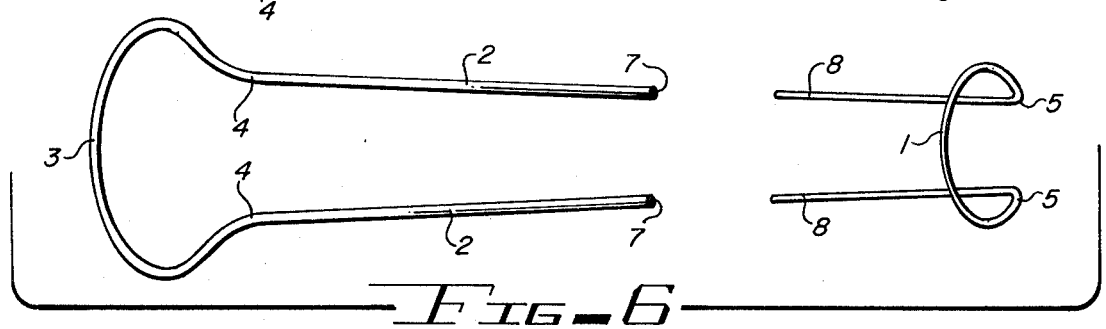

PENILE SUPPORT

This is a continuation-in-part of my patent application, Art Unit 335, filing date of 16 January 1979, Ser. No. of 12,836, which was a continuation-in-part of my original patent application, Art Unit 335, filing date of 18 December 1978 and Ser. No. 970,490, now abandoned.

PRIOR ART STATEMENT

The wire splint described by Loewenstein of London, England in 1947 and, at that time, made by Down Bros., British patent unknown. This is a multiple hinged and multiple jointed splint with a proximal elastic accumulator attached to projecting ventral arms which transmit contracting force along the ventral supports to the distal loop.

U.S. Pat. No. 1,153,072 discloses a sleeve-like body having longitudinally disposed slits for flexibility. This splint completely encircles the penis and is made from rubber to render the splint flexible and resilient.

U.S. Pat. No. 3,131,691 describes a proximal and distal web with a cradle on the undersurface and a strut on the opposite surface. The cradle has a body of soft surgical rubber. Imbedded within is a concave steel reinforcement.

U.S. Pat. No. 1,585,861 discloses an elongated member made of a sufficiently rigid material to meet all requirements. Concave in cross-section extending less than a semi-circle and lies mostly ventrally and is held in place by elastic bands. The sides are firmly united to each other both distally and proximally.

U.S. Pat. No. 844,798 discloses stiffening members extending on opposite sides of the organ. Elastic web-like connection distally to encircle the corona. An elastic jacket encircles the device to keep it in position.

U.S. Pat. No. 3,401,687 teaches a longitudinally splint tube made of a flexible material with a light spring action. This is completely surrounded by an elastic cover.

U.S. Pat. No. 1,216,099 discloses the support which is a split sleeve of rubber and it encloses the organ. Each side of the splint has a series of perforated lugs and an engagement rod for fixation.

U.S. Pat. No. 3,495,588 discloses a surgical splint comprising a unitary flexible and rigid tubular shank open at both ends and open along its side to aid in extraction during copulation.

U.S. Pat. No. 3,820,533 discloses an inflatable ring at the base for compression and a tubular sleeve portion.

U.S. Pat. No. 3,982,530 discloses at least four supporting ribs extending proximally from the distal base. The male organ is completely encased. It is made from a thin relatively rigid material such as a plastic or metal sheet with a plastic coating.

U.S. Pat. No. 1,346,463 discloses a pair of elongated thin flat metallic bars joined proximally by a spring yoke and distally by a spring ring; the splint is formed of a spring metal or equivalent material. In the main splint there are several sustaining elements proximally. In the modified splint, the distal loop is hinged.

It is not believed that any of the devices described in the foregoing patents are satisfactory for the following reasons.

The wire splint by Loewenstein has multiple hinges, it is rigid and clumsy, and the distal loop conforms in no way to the coronal sulcus of the penis and only grips it at all by virtue of a proximal rubber band accumulator.

U.S. Pat. No. 1,153,073 discloses a device which completely encloses the shaft of the penis and appears difficult to apply. It is made from rubber.

U.S. Pat. No. 3,131,691 shows a ventral cradle and a dorsal strut. There is insufficient exposure of the shaft of the penis and the splint would be difficult to apply due to the presence of proximal and distal webs. There is flexibility but not malleability of the device.

U.S. Pat. No. 1,585,861 discloses the importance of its use for non-sexual purposes as opposed to sexual purposes is stressed, and when used for the latter purpose, it is inadequate for the following reasons. The ventral longitudinal support is a single unit with a longitudinal slit in the center of its long axis, it is semi-rigid and nonadjustable laterally, its proximal end abuts against soft tissue and therefore there is no thrust, the proximal band and more especially, the distal band, is inadequate for fixation with this single ventral support.

U.S. Pat. No. 844,798, by Hawley in 1907, discloses two lateral supports which are too wide and would thus prevent adequate contact between the penis and vagina. The whole splint is covered with an elastic jacket which would further limit contact with a vagina. The tight rubber opening distally could make it difficult to insert the glans penis through the opening.

U.S. Pat. No. 3,401,687 discloses a plastic support completely encircling the shaft of the penis with resulting poor contact between the penis and the vagina. An elastic cover is used, further limiting contact.

U.S. Pat. No. 1,216,099 discloses a splint sleeve of rubber joined by lugs. It is altogether too complex and entirely surrounds the shaft of the penis.

U.S. Pat. No. 3,495,588 discloses a removable tubular shank enclosing the ventral and lateral aspects of the penis. Too much of the shaft of the penis is covered by a rigid material.

U.S. Pat. No. 3,920,533 discloses a too complicated device with an inflatable ring at the base. Is made of relatively rigid or flexible plastic material.

U.S. Pat. No. 3,982,530 discloses that the penis is completely enclosed and the glans penis does not project beyond the end of the splint and therefore does not make adequate contact with the vagina. Formed from a thin relatively rigid material such as a plastic or metal sheet with a plastic coating. This splint could produce trauma to the vagina.

U.S. Pat. No. 1,346,463 by Renois in 1920, discloses two splints, the main splint and the modified splint. In the main splint there are several sustaining elements proximally and these could well irritate the vaginal outlet during use, especially anteriorly where these sustaining elements approach each other at a sharp angle. In the modified splint, the distal spring ring is hinged. This would lead to inadequate fixation, more especially so as no distal locking band is used. As the splint is formed of spring metal or equivalent material, there are no means of lengthening or shortening the support, and the distal head piece and the proximal end are not fully adjustable. There is no added fixation as an elastic member for the head piece.

My support is dissimilar for the most part from other penile supports mentioned in the prior art. The support by Renois has a superficial resemblance to mine, but due to the fact that his support is made of spring metal or equivalent material and mine of a malleable material, whether that be metal or plastic, makes all the difference.

SUMMARY OF THE INVENTION

A malleable clip-on self-retaining endless outline penile support, used to make the sexual act possible in the case of male weakness. The device consists of a malleable adjustable head piece joined by two less malleable longitudinal supports which join proximally a looped-shaped proximal portion which extends proximally and dorsally to surround the sides and dorsum of the base of the penis, and in so doing, the proximal portion of the support will come to rest in front of the tissues, in front of the symphysis pubis when in use.

Malleability transversely of the proximal part of this looped-shaped proximal portion permits adjustment of the proximal ends of the longitudinal supports, and a malleable angle towards the proximal end of each longitudinal support at the junction with the proximal looped-portion of the support enables the length of the penile support to be varied.

Additional fixation distally is achieved by an elastic member and a second such member can be used proximally. Safety extraction in case of dislodgement of the support is achieved by the use of anterior posterior elastic members or by the fact that the head piece is capable of acute distal flexion. The support may be encased in plastic, preferably plastic tubing.

DETAILED DESCRIPTION OF DRAWINGS

The foregoing and further and more specific objects and advantages of the instant invention will become readily apparent to those skilled in the art from the following detailed description of preferred embodiments therefor taken in conjunction with the drawings, in which:

FIG. 1 is a perspective view of a penile support constructed in accordance with my invention;

FIG. 1A is an enlarged cross-section taken along the line of 1A of FIG. 1;

FIG. 2 is a plan view of the support of FIG. 1, being shown in an open position;

FIG. 3 is a plan view generally corresponding to the illustration of FIG. 2 but shown in the closed position with a proximal fixation band;

FIG. 4 is a side view of the device of FIG. 3 showing sharp angulation forwards of head piece, also showing is an optional elastic member;

FIG. 5 is a plan view of a type of malleable support prior to moulding into the final support;

FIG. 6 is a plan view of an alternate type of a malleable support during an intermediate phase of development;

Figure 7A:
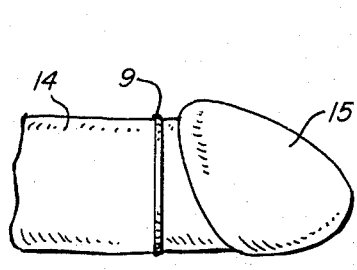
FIGS. 7A–7C and FIG. 7E are lateral views of the distal penis showing in sequence one method of additional fixation utilizing an elastic member.

Turning now to the drawings in which like reference numerals indicate corresponding elements throughout the several views, attention is first directed to FIG. 1 which shows an outline malleable penile support consisting of a head piece 1 and two longitudinal supports 2. The head piece 1, due to its malleability and ventral opening, can be made to conform to the shape, size and angle of the coronal sulcus of the penis and has a variable grip which helps to prevent distal displacement during use. The two ventral longitudinal supports 2 join the open ventral part of the head piece 1 and here make a distal angle 5. The longitudinal supports 2 extend proximally and here join a generally loop-shaped proximal portion which embraces the base of the penis. At the site of the junction is an angle and due to its malleability, this angle can be increased or decreased and by so doing the length of the penile support can at the same time be increased or decreased. The malleability of the proximal loop enables the loop, more especially its sides and the proximal parts of the longitudinal supports, to be adjusted. Added fixation of the head piece 1 is achieved by the use of an elastic member 9 of about size twelve. The proximal looped portion can also be made adjustable lengthwise with the longitudinal supports.

There are two methods of application. In the first method, shown in FIGS. 7A–7E, an elastic member 9 is first passed around the distal part of the shaft of the penis 14. The support is then applied and the central dorsal part of the elastic member is first pulled up and then pulled over the transverse portion of the head piece 1, and the glans penis 15. The elastic member is now forcibly pulled forwards to make it engage through the ventral angles of the head piece. The elastic member is now twisted 90° and the distal loop 11 so formed is lifted upwards and so over the glans penis 15 and then either distal to or proximal to the transverse portion of the head piece 1 of the support, the elastic member then encircles the coronal sulcus or the adjacent part of the shaft of the penis. In so doing, it passes either distal to or proximal to as shown in FIG. 7E. The ventral angles 5 of the head piece 1, if proximal, it will also pass over the distal part of each longitudinal support 2.

Figure 7B:
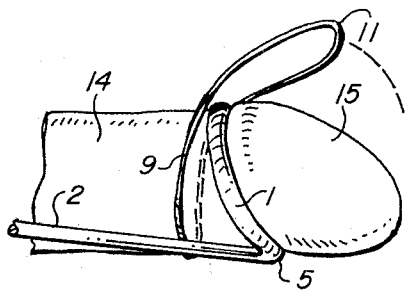
Figure 7C:
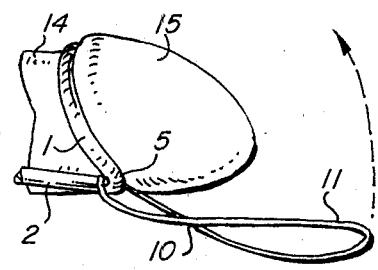
Figure 7D:
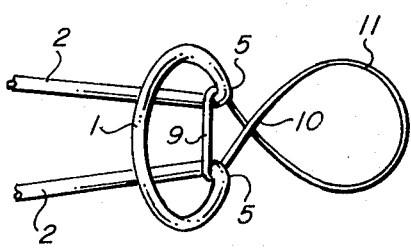
FIG. 7D is a plan view illustrating the step intermediate the steps illustrated in FIGS. 7C and 7E, the penis being removed for purposes of illustration.
Figure 7E:
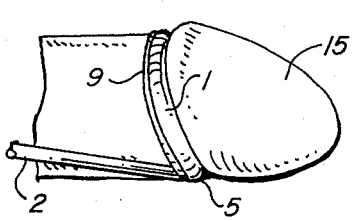
Figure 8A:
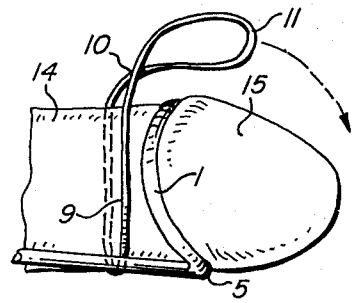
FIG. 8A is a lateral view of the distal penis illustrating an alternate method of distal fixation.
Figure 8B:
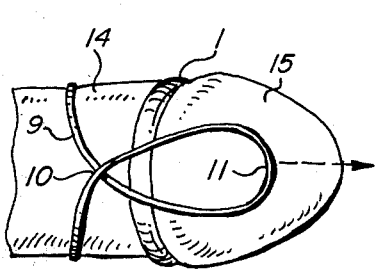
FIGS. 8B and 8C are dorsal views of distal penis, corresponding to the view of FIG. 8A and illustrating sequential additional steps of the method thereof.
Figure 8C:
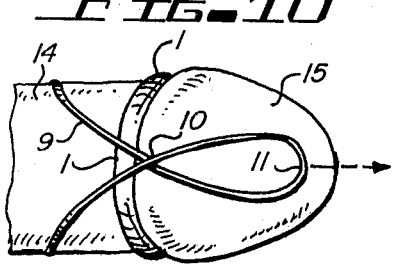

In the second method of fixation shown in FIG. 8, the initial procedures depicted in FIGS. 7A and 7B are the same but the final procedures are different and here the 90° twist is either made before or after crossing the transverse portion of the head piece 1, the distal loop 11 of the elastic member 9 is then lifted over the glans penis 15 and then made to lodge in the coronal sulcus.

Figure 9A:
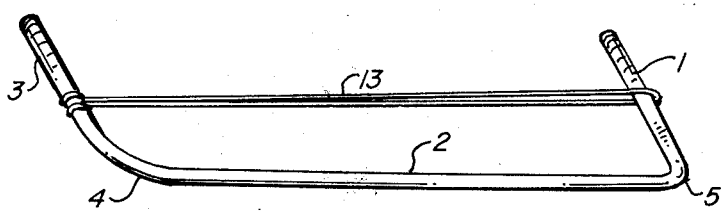
FIG. 9A is a lateral view of a support of the instant invention illustrating an optional additional elastic member.
Figure 9B:
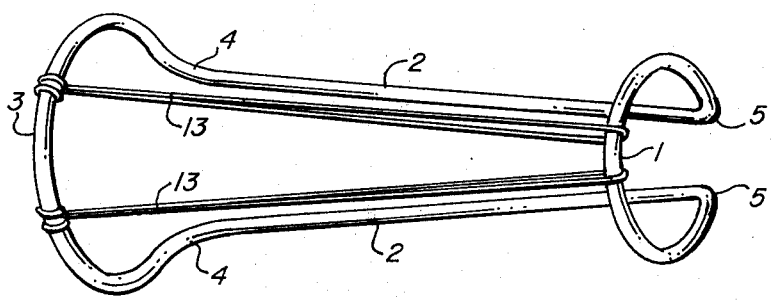
FIG. 9B is a plan view of the embodiment illustrated in FIG. 9A.

A special safety measure for extraction of the splint should slipping forwards occur, is provided by two elastic members 13 as shown in FIG. 9B, one on each side fixed proximally to the proximal part of each longitudinal support 2 and looped over the head piece 1 of the support distally. This is shown in a lateral view in FIG. 9A and a plan view FIG. 9B.

Figure 10:
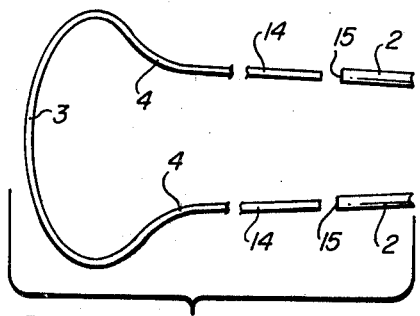
FIG. 10 illustrates a modification of penile support illustrated in FIG. 6.

In the penile support of FIG. 10, the proximal loop-shaped portion 3 is made of malleable soft steel wire of suitable tensile strength and size of about 16 gauge so that its distally projecting ventral end 14 of about 2 inches long can be received into the hollow proximal end 15 of the longitudinal support 2. The longitudinal supports 2 in this case are still hollow as in the original support but as they are not continued as such into the proximal looped portion 3 they can thus be made of the same malleable material but can also be made of a semi-rigid material which would include metal and plastic. The length of the distally projecting free ends 14 of the proximal portion of the support which is received into the proximal ends 15 of the longitudinal supports 2 is variable as is also the site of proximal angulation 4. This enables the length of the support to be varied by simply pulling out the proximal end to make longer and pushing in to make shorter, the proximal angle 4 being reformed at the same time. The covering plastic tubing will accommodate itself to any change of length by virtue of its elasticity. In this support with its increased proximal flexibility lateral adjustment of the proximal part of the longitudinal supports is more readily made. The method of changing the length of the support is only secondary to the method in which the degree of angulation of the proximal angle 4 is altered, and should not be used routinely. Further fixation of the proximal part of the supports to prevent dislodgement of the support during use is achieved by an elastic member 16 of about size 10 which helps to keep the proximal ends of the longitudinal supports together in the region of the proximal angles 4. This is achieved by first applying the elastic member of the shaft of the penis and then after applying the support lifting up the center portion of the dorsal part of the elastic member over the glans penis illustrated in FIG. 7B and then pulling it proximally and ventrally so as to enable it to lie in its position of use embracing the proximal ends of the two longitudinal supports.

In the preferred embodiment of my invention, I have also made use of the following devices.

In FIG. 5, the malleable material now used in the construction of one of my support is soft annealed stainless steel wire of about 15 to 16 gauge with a tensile strength of 80,000 to 120,000 pounds per square inch. This strength and thickness is now thought necessary for the longitudinal supports 2 to prevent bending during use, ad the malleability of the head piece 1 of the support is quite satisfactory, though more malleatility would be an improvement and one method of achieving this is as follows:

In FIG. 6, a piece of brtass tubing about 11 inches long with an outside diameter of 3/32 of an inch and an inside diameter of 1/16 of an inch containing a wire within its lumen to prevent kinking when bent and to add to its strength. This is moulded into the proximal curved part 3 and the straight ventral parts of the longitudinal supports 2. The distal inch and a half or so of these longitudinal supports remain patent and the open ends 7, as viewed in FIG. 6, here receive the free proximally projecting ends 8 of the head piece 1 either made of 17 gauge soft stainless steel wire when some limited malleability is preferred and of 19 gauge galvanized iron wire when more malleability is preferred, more especially so in contributing to a safety device as under these conditions the head piece 1 of the support can be flexed acutely forwards and thus avoid any catching on a vagina in the event of extraction of the splint following slipping forwards of the distal end.

The malleability of the head piece 1 is of importance and if 19 gauge galvanized wire is used, there can be very little grip by the head piece 1. The wire thus acts as a sling, the gripping force being transmitted along the longitudinal supports from the more resilient proximal part of the support. Furthermore, when in use, the tight fit and contractions of a vagina will press together the distal comparatively unhampered ends of the longitudinal supports and thus tighten the grip of the head piece around the coronal sulcus of the penis. This sling device further prevents distal displacement of the head piece. When 17 gauge soft annealed stainless steel wire is used for the head piece, there is an added gripping force but most of the factors mentioned above also come into play in preventing displacement of the head piece of the support forwards during use.

The support is now covered with a plastic tubing and under these conditions, the size of the head piece can still be adjusted by pulling out or pushing in the proximally projecting portions as seen in FIG. 6 of the head piece 1. Further fixation of the proximal end of the support can be achieved by an elastic member 17 as seen in FIG. 4 fixed on either side to the proximal part of each longitudinal support and then after looping over the distal part of the penis is made to lodge in the perineum behind the scrotum. The support with the less malleable longitudinal supports and the more malleable head piece is now the support of preference. When the less malleable head piece is used as is now the case, in the all wire supports, the distal elastic member adds elasticity as well as security to the support.

Having fully described and disclosed the present invention and alternately preferred embodiments thereof in such clear and concise terms as to enable those skilled in the art to understand and practice the same, the invention claimed is:

1. A penile support for engagement with the male organ and for assisting in the sexual function in case of male weakness, said support comprising:
   a. a pair of malleable spaced apart elongated longitudinal supports for supporting and extending the ventral surface of the penis, each said support having a distal end and a proximal end;
   b. a malleable, generally loop-shaped, proximal portion integrally joining the proximal ends of said pair of supports and extending upwards therefrom over said male organ,
      said proximal portion being deformable relative said longitudinal support for selectively varying the angular relationship between said proximal portion and said pair of supports,
      the said proximal portion being further deformable to enable adjustment of adjacent longitudinal support transversely; and
   c. a malleable head piece extending between the distal ends of said pair of supports and having a curve therein for extending upwards over coronal sulcus of said male organ,
      said head piece being more malleable than said longitudinal supports.

* * * * *